United States Patent [19]

Nees

[11] Patent Number: 4,542,101
[45] Date of Patent: Sep. 17, 1985

[54] PROCESS FOR THE CULTIVATION OF MATRIX-BOUND BIOLOGIC CELL SYSTEMS

[76] Inventor: Stephan Nees, Waldwiesenstrasse 30b, 8000 Munchen 70, Fed. Rep. of Germany

[21] Appl. No.: 428,023

[22] Filed: Sep. 29, 1982

Related U.S. Application Data

[62] Division of Ser. No. 180,035, Aug. 21, 1980, Pat. No. 4,373,029.

[30] Foreign Application Priority Data

Aug. 24, 1979 [DE] Fed. Rep. of Germany ....... 2934328

[51] Int. Cl.[4] .......................... C12N 5/00; C12N 5/02; C12M 3/00
[52] U.S. Cl. .................................. 435/240; 435/241; 435/284
[58] Field of Search ............... 435/240, 241, 284, 285, 435/286

[56] References Cited

U.S. PATENT DOCUMENTS

| | | | |
|---|---|---|---|
| 3,717,551 | 2/1973 | Bizzini et al. | 435/241 |
| 3,893,887 | 7/1975 | Smith et al. | 435/284 X |
| 3,905,865 | 9/1975 | McAleer et al. | 435/240 X |
| 4,036,693 | 7/1977 | Levine et al. | 435/240 |

Primary Examiner—Robert J. Warden
Assistant Examiner—Randall E. Deck
Attorney, Agent, or Firm—Peter K. Kontler

[57] ABSTRACT

Improved process for cultivation of matrix-bound biologic cell systems on microcarrier particles within a replenishable nutrient medium including the step of providing controlled three dimensional displacement of a culture vessel and its contents to effect uniform cell exposure to available nutrient material.

6 Claims, 8 Drawing Figures

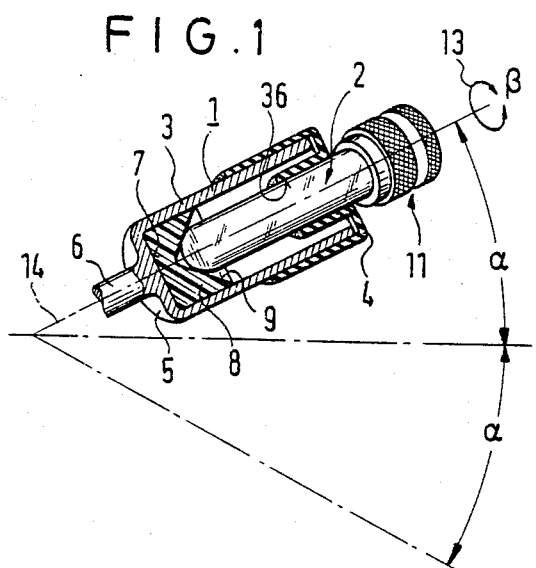
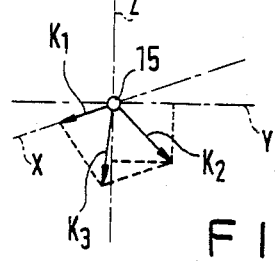
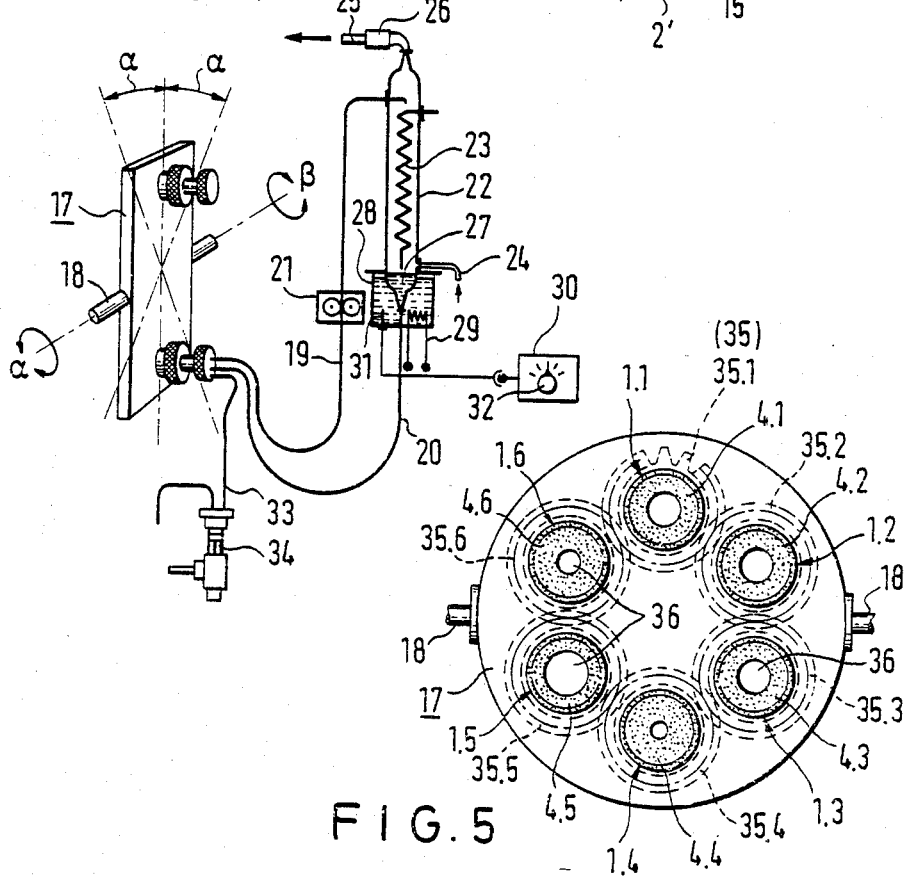

PROCESS FOR THE CULTIVATION OF MATRIX-BOUND BIOLOGIC CELL SYSTEMS

This is a division of application Ser. No. 180 035 filed Aug. 21, 1980 now U.S. Pat. No. 4,373,029.

BACKGROUND OF THE INVENTION

The invention relates to a process for the cultivation of matrix-bound biologic cell systems, such as bacteria, fungi, mammalian cells and the like, on microcarrier particles that are selectively displaced within a replenishable nutrient medium in a confined area to provide for uniform exposure of the cell systems to available nutrient material.

As is known, the cultivation of matrix-bound biologic cell systems may conveniently take place (for example, see Lewis et al.: 2nd Gen. Meeting ESACT, June 23–26, 1978 or Levine et al.: Somatic Cell Genetics 3(2):149–155, 1976) on microcarriers in the form of carrier particles having a specific gravity close to the reference magnitude of 1 g/cm$^3$, e.g. gel beads, suspended in a nutrient medium forming an environmental atmosphere suitable for the fermentation of the culture in each case. For a uniform supplying of the culture with nutrient substrates and oxygen, such suspension is contained in a culture vessel and displaced during the fermentation either by displacement of the culture vessel or by displacement of the contained suspension by means of internal mixing elements, by a back-and-forth or rotating movement. An attempt is thereby made to apply the nutrient solution and the oxygen as uniformly as possible to the culture that is spreading on the surfaces of the microcarriers. Such known process for the cultivation of matrix-bound cell systems on microcarriers freely suspended in a nutrient medium is generally employed at the present time despite its disadvantages or deficiencies as hereafter pointed out.

Thus where the suspension is directly kept in motion by mechanical mixing elements, for example by magnetic agitators, perforated disks moving back and forth, or the like, an abrasion or shearing of cells of the culture spreading on the surface of the microcarriers is unavoidable. The magnitude of the shearing forces is generally proportional to the intensity of the agitation. Such shearing forces however not only act disadvantageously on the culture but cause electrostatic charges to develop in the system, as well as inducing foaming of the protein-containing nutrient medium when the culture is supplied with oxygen at the same time. Additionally, the supplying of the cells with nutrient materials is also thereby impaired. Even if great care is taken, it is scarcely possible to avoid the entry of foreign substances into the suspension with the use of such mixing elements, so that the sterility of the culture is no longer assured.

It is apparent that these mechanical mixing disadvantages may be partly avoided if such direct contact mechanical mixing elements are dispensed with and, as known, the culture vessel is put into a rolling or back-and-forth movement. However, a disadvantage which then arises in this case is that in such one-or two-dimensional movements, the microcarriers do not get to float and thereby loosen away from the vessel walls; that is they always remain in the lowest level of the vessel, even though their motion is a "rolling" one. A reciprocal contact here, too, leads to abrasion of the cultures; in addition, a uniform supplying of the cultures with the nutrient medium and with oxygen is no longer assured under these conditions.

OBJECTS AND SUMMARY OF THE INVENTION

The goal of the invention is therefore to provide an improved process for effecting the uniform supplying of nutrients to microcarrier supported cell cultures that avoids the disadvantages mentioned above as much as possible. In its broad aspects, the subject process avoids the use of direct contact mixing elements and provides a three-dimensional movement of the culture bearing microcarrier within the suspension, where the microcarrier acceleration magnitudes are essentially determined only by the gravity of the microcarrier in the earth's gravitational field, reduced by the viscosity of the nutrient solution. Among the advantages attendant the practice of the invention is a marked reduction in abrasion, a permitted foam-free freshening of the nutrient solution and enhanced uniformity of exposure of the culture to the nutrient medium.

Due to the fact that the culture vessel which is normally completely filled with nutrient liquid, and is preferably designed as a round flask, is both pivotally and rotatably displaced at the same time, there is a uniform exposure of the individual microcarrier particles within the culture vessel to the nutrient medium without foaming; the swinging and rotating amplitudes may be varied and adjusted according to the culture in each case as well as the swinging and rotating frequency. It is thereby possible to determine and then establish the optimum conditions for the nutrient exposure in each case, for example by occasionally taking samples from the vessel. The suspension is covered or shut up in the culture vessel so that no microorganisms are able to penetrate into the culture vessel from outside. There are no mixing elements extending into the suspension, so that no excessive shearing forces destructive to the culture can develop. In order to keep the nutrient medium in an oxygen enriched state during the fermentation, the nutrient medium is withdrawn constantly or in stages by way of a sterile filter during the swinging and rotating movement, and it is at the same time replaced by oxygenated or refreshed nutrient medium. In order for the gel beads bearing the cells and which are retained freely suspended in the culture liquid not to undergo any injurious accelerations and electrostatic charges or any excessively great reciprocal abrasion, it is essential to limit acceleration to a maximum of 0.3 m/s$^2$ and above a minimum of 0.002 m/s$^2$. The particular acceleration magnitudes to be employed depend on the type of carrier particles and they must be determined by preliminary experiments.

The apparatus for the practice of the novel process includes a housing member having a longitudinal axis and a culture vessel removably insertable therein in association with means for effecting a conjoint controlled pivotal and rotational displacement of the housing member and contained culture vessel. In particular, this apparatus is suitable to accommodate culture vessels of different sizes. It is to be considered in this connection that the device is to be operated in culture or climatized cabinet protected against light and means are provided to permit rapid and convenient removal and replacement of culture vessels even during the operation of the device. Means are also provided to permit feeding and withdrawal of the nutrient medium solution into and out of the culture vessel chamber and a taking of samples from the culture vessel or vessels during the operation of the device must be possible, even if the latter is located within a culture cabinet. Of course, the line leading to the culture vessel or vessels should not become twisted during the operation of the device and visibility of the working field of the device must always be assured.

A plurality of culture vessel containing housing members can be mounted in parallel spaced relation on a common support wherein pivotal displacement of the support effects simultaneous pivotal displacement of all the culture vessels. Concurrently therewith all of the culture vessels are simultaneously rotated in an oscillatory pattern. Due to the swinging or pivotal movement of the support plate in connection with the oscillatory rotary displacement of the culture vessels, the desired three-dimensional movement of the microcarriers within the culture liquid is achieved, and accordingly produces a good uniform diffusion exchange of nutrient substances and metabolites with an avoidance of undesired shearing forces. Twisting of the lines leading to the culture vessel is avoided by the back-and-forth swinging movement of the pickup device for the culture vessel.

It is especially advantageous if the device is designed to receive several culture vessels, suitably of the cylindrical flask type, and in the process the movement amplitudes and frequencies for the common support plate on the one hand and for the housing members for the culture vessels to be maintained adjustable. The adjustment of the movement amplitude for the support plate is achieved by adjusting the tipping angle, whereas the adjustment of the angle of rotation of the receiver device is the measure of the oscillation amplitude. The drive engine is connected to an infinitely variable speed transmission. The number of revolutions set at the transmission gives the oscillatory frequency of the driven machine parts in each case.

The material of the culture vessels must be impermeable to UV light; it should have a slight adhesion for the microcarriers. In addition, the culture vessels must be easy to handle, rapidly closable, and must be without problems with respect to their sterilization.

The inventive process is illustrated further below with the aid of the drawings, as well as a device serving for the utilization of the process in addition to some details.

BRIEF DESCRIPTION OF THE DRAWING

FIG. 1 is a perspective sectional view of the housing member for a culture vessel;

FIG. 2 shows the movement components of a carrier particle in a coordinate system;

FIG. 3 is an enlarged fragmentary transverse sectional view of a culture vessel;

FIG. 4 is a schematic partly elevational, partly perspective and partly sectional view of an apparatus for the practice of the process;

FIG. 5 is an enlarged front elevational view of a plate-like support for several housing members;

DESCRIPTION OF THE PREFERRED EMBODIMENTS

Figure 6:
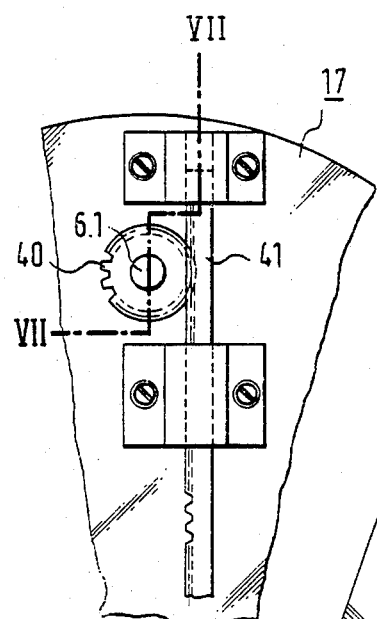
FIG. 6 is a fragmentary elevational view of a drive system for the support.

FIG. 1 shows receiver device or housing member 1 for culture vessel 2. The housing member consists of basin or cylindrical sleeve 3 on which a collar ring 4 made of an elastic material is placed. Basin 3 possess turning tap or stud 6 at the end turned away from the collar ring. In floor 7 of the basin there is support pad 8 with conical part 9 as a stop for the ball end of the culture vessel designed in the form of a cylindrical flask. By a pull in the direction of arrow 10, the culture vessel can be removed from the basin rapidly and safely, and if desired it can again be introduced or exchanged for another culture vessel. The suspension consisting of nutrient solution and the carriers bearing the culture, among other elements, are located in the culture vessel. At its head end, the culture vessel bears closure head 11 with inset head 12 (see FIG. 8) to take up feed and withdrawal lines. In order to assure a uniform supplying of the culture with the nutrient medium and oxygen, the suspension located in the culture vessel is swung in a vertical plane upward and downward by angle $\alpha$ about a horizontal axis in each case; at the same time, oscillatory rotative displacement of the culture vessel around its longitudinal axis 14 takes place back and forth as indicated by arrow 13.

The movement conditions of the suspension resulting from this are represented in FIGS. 2 and 3.

FIG. 2 shows the movement components of a carrier particle (carriers) 15 floating in the suspension in an orthogonal coordinate system. If the culture vessel is swung from raised position into low position according to the representation in FIG. 1, a movement running in the direction of component $K_1$ is forced on the carrier particle both by the force of gravity and due to the centrifugal force appearing as a result. By rotating the culture vessel around its longitudinal axis, a rotary movement is also forced on the suspension, caused by wall friction. As a result, the carrier particle also attempts to migrate in the suspension in the direciton of component $K_2$. Components $K_1$ and $K_2$ give resulting component $K_3$. The particle or the mass of all particles accordingly carry out a spatial movement within the culture vessel. In the process, it is essential for the swinging movement of the culture vessel to take place upward and downward from the middle position, thus oppposite to and in the direction of the acceleration due to gravity.

FIG. 3 shows a radial cross-seciton through the culture vessel. When rotation is started or there is a reversal of the rotation direction of culture vessel 2, the layers of suspension 16 near wall 2' are first entrained, whereas the layers distant at a radial interval still persist in the prior direction of rotation for some time after the reversal of the direction of rotation. This results in a weak whirling formation in the "neutral ring zone" slowly penetrating inward from the periphery, so that carrier particles 15, as represented, undergo a good but protective bathing in the nutrient medium in this whirling. Care is thereby to be taken that both the acceleration and retardation conditions of the swinging and rotary movements remain within the given limits.

FIG. 4 shows the design of the device for the utilization of the process in a schematic representation. Receiver devices or housing members 1 to receive culture vessels 2 are attached to swinging plate 17 at a suitable distance from its swinging axis 18. As will later be discussed, a back-and-forth or oscillatory rotary movement of the receiver devices and contained culture vessels about their longitudinal axis is achieved by a suitable drive mechanism conjointly with the swinging movement of plate 17. As is seen, thin tubes or lines 19, 20 are passed through insert body 12 of culture vessels 1. The nutrient medium is passed through line 19 for the purpose of replenishing with oxygen by intermediate connection of hose pump 21 to oxygenator 22. The nutrient medium here flows to coil 23 from above downwards. In the opposite direction, and accordingly in countercurrent to the nutrient medium, oxygen is passed through the oxygenator; oxygen feed takes place at 24 and withdrawal is at 25. Valve 26 is placed in the outlet connection piece; it is designed to open only at an excess pressure of about $10^{-2}$ bar, and otherwise it is closed below that pressure. A sterile atmosphere within the oxygenator should thereby be assured and the penetration of foreign microorganisms excluded. The nutrient medium enriched with oxygen reaches the collector part 27 of the oxygenator and flows by the force of gravity and supported by the prevailing reduced pressure produced in the culture vessel by pump 21 replenished or enriched with oxygen back into the culture vessel through line 20. The device will usually be arranged within a conditioning cabinet during the fermentation, whereas the oxygenator is located outside the cabinet. A cold shock in the return of the refreshed culture medium to the culture should be avoided, and for the purpose collector part 27 of the oxygenator is surrounded by tempered bath 28; the bath is supplied with heating 29. The heating can be regulated by means of thermostat switch 30 in connection with heat sensor 31. As is usual in such devices, adjustment of the desired temperature takes place at handle 32. Another line 33 which is connected with flask buret 34 is passed through insert body 12 of culture vessel 2. When the buret is activated, a small measured quantity of the suspension is removed from the culture vessel as a sample.

FIG. 5 shows a preferred design of swinging plate 17 with a number of receiver devices or housing members 1 mounted thereon. According to the example, six receiver devices 1.1 to 1.6 each capable of rotation are attached to a swinging plate 17 of circular design. The rotating studs 6 of the receiver devices each bear a gearwheel 35, all of which mesh with each other, as represented. If one of the gearwheels is driven the other gearwheels also rotate and with them the pertinent receiver devices. Insertion openings 36 in collar rings 4.1 to 4.6 for the culture vessels can be designed in different sizes, so that they are suitable for receiving culture vessels of different diameters and therefore also volumes from the ml to the liter range. The device can be used for both laboratories and for commercial operation.

Figure 7:
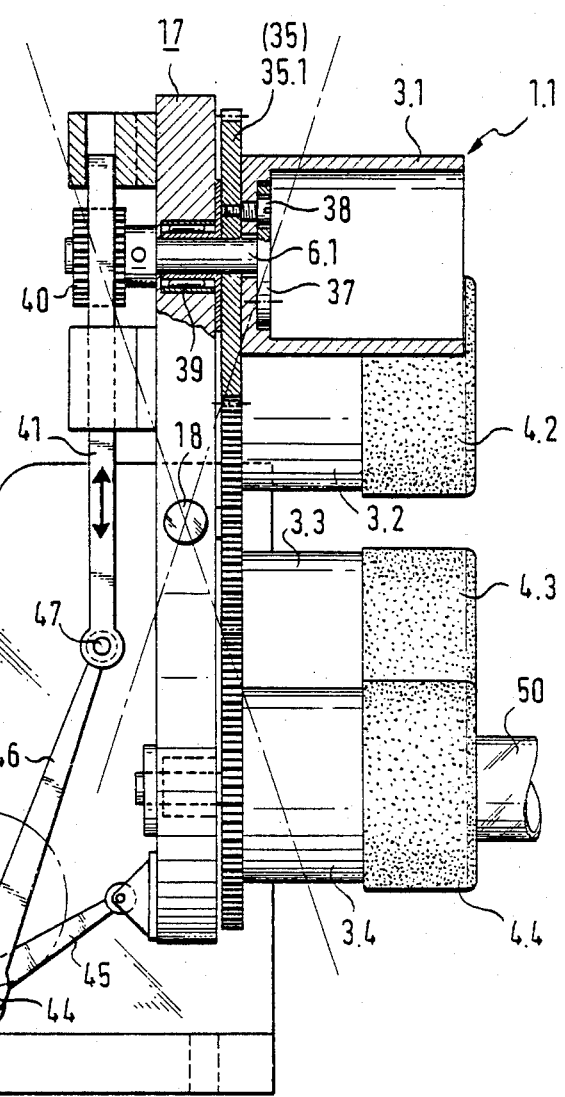
FIG. 7 is a sectional view as seen in the direction of arrows from the line VII—VII of FIG. 6.

FIGS. 6 and 7 show a preferred drive system of the device, where FIG. 6 represents a section of the rear view of the device in FIG. 7. Rotatable stud 6.1 terminates in flange 37 which is connected by bolt 38 to the gearwheel 35.1 through the base wall of the housing member. The rotatable stud 6.1 is supported in needle roller bearing 39 in the swinging plate 17 and has pinion 40 mounted at its terminal end with which rack 41 meshes. As will be apparent lineal reciprocation of the rack 41 effects a concomitant rotative displacement of the housing member 3.1 around its longitudinal axis, and with the angle of rotation being proportional to the amplitude of rack displacement and the rate of rotation being proportional to the rack displacement rate. Because all receiver devices 1.1 to 1.6 are in meshing state with their gearwheels, they follow the first-mentioned receiver device in their movement. For the purpose of a clearer representation, receiver devices 1.5 and 1.6 are not represented in the drawing in FIG. 7; however, the arrangement is seen from FIG. 5.

Steering arm or connecting rod 45 and connecting rod 46 are linked to pivot 44 at crank arm 42, which is driven by rotatable shaft 49 connected to a prime mover or an engine whose speed is capable of being regulated in the rotary direction indicated by arrow 43. The steering arm 45 is in flexible or pivotable connection with swinging plate 17, whereas the connecting rod 46 is connected with rack 41 by crosshead 47. The crank arm 42 is rotated, the swinging plate 17 is swung around its swinging axis 18, whereby at the same time the receiver devices are driven by means of the connecting rod 46 and rack 41. Instead of connecting rod 45, a cam plate can also be used, which is either also arranged on shaft 49 or has its own drive. Such a cam plate is to be preferred if the swinging movement of the swinging plate 17 is to have a path of displacement diverging from the sine wave form. The regulation of the number of revolutions for the motor driving shaft may take place either electronically by controlling the number of revolutions of the engine or by a connected gear capable of regulating the number of revolutions. Regulation of angle of swing and angle of rotation takes place by dimensioning the interval (eccentric measure) of pivot 44 from the rotation axis or by displacement and fixation of the pivot in longitudinal slot 48 of crank rocker arm 42.

Figure 8:
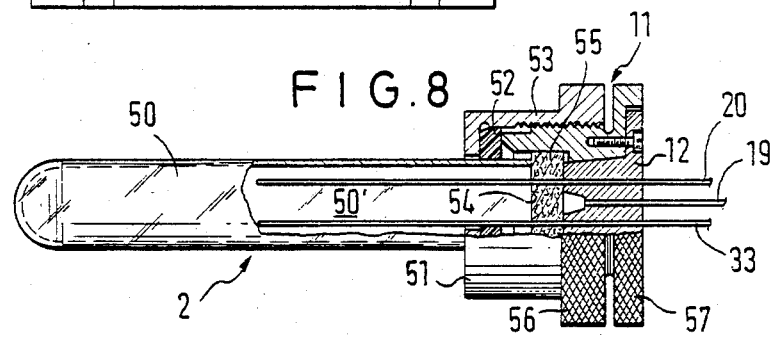
FIG. 8 is an enlarged partly elevational and partly sectional view of a culture vessel.

FIG. 8 shows the design of culture vessel 2 such as is advantageously used with the device. It consists of a cylindrical body 50 designed as a test tube which is closed by means of closure head 11; the latter consists of screwed cap 51, ring washer 52, and gland ring 53. Filter 55 rests against open end wall 54 of the body; it is retained by insert body 12 passed into the gland ring. Thin plastic lines (tubes) 19, 20 and 33 are passed through the insert body, whereby lines 20 and 33 penetrate into the glass body, whereas line 19 is located behind filter 55. If space 50' is filled with the suspension, consisting among other elements of microcarriers and the culture, not represented here, and if a vacuum is now applied to line 19, only the liquid nutrient medium flows through filter 55, whereas the carriers (carrier particles) bearing the culture are retained. As already described above, the nutrient medium conducted to the oxygenator 22 (FIG. 4), and after it is freshened up it is again conducted to the culture space through line 20.

Line 33 serves for taking a culture sample, as also described above. Gland ring 53 is screwed off to open the culture vessel, so that the glass body is now free. For better handling of the culture vessel in filling and emptying, tops 56 and 57 of screwed cap 51 and gland ring 53 are knurled.

The process can be altered in many ways within the framework of the characteristics of the invention. Receiver devices 1 can thus be arranged at a swinging band in a row or on a plate in files and columns. The drive of the swinging plate, especially in large installations, can be attained separately from the drive of the receiver devices. A possibility also exists of providing the swinging plate and thereby also the receiver device with its culture vessels with a heatable or temperable cap without thereby departing from the framework of the invention. The expression "swinging plate" used can include any other construction serviceable to experts; for example, it can also be a framework or latticework.

I claim:

1. Process for the cultivation of matrix-bound biologic cell systems on microcarrier particles in a nutrient medium which is confined in a culture vessel, comprising the steps of imparting to the culture vessel and its contents a back-and-forth movement about a first axis; simultaneously imparting to the culture vessel a back-and-forth rotary movement about a second axis; and freshening the nutrient medium by oxygenation.

2. The process of claim 1, wherein said freshening step includes freshening the nutrient medium in batches.

3. The process of claim 1, wherein said freshening step includes constantly freshening the nutrient medium.

4. The process of claim 1, wherein said movement imparting steps include accelerating the microcarrier particles to between 0.002 and 0.3 m/s$^2$.

5. The process of claim 1, wherein said freshening step comprises filtering the nutrient medium from the culture vessel by suction while the culture vessel is in motion, oxygenating the filtered nutrient medium in a sterile tempered atmosphere which is enriched with oxygen, and returning the oxygen-enriched nutrient medium into the culture vessel.

6. The process of claim 1, further comprising the step of removing some of the contents of the culture vessel as a sample.

* * * * *